United States Patent [19]

Aoshima et al.

[11] 4,446,328

[45] May 1, 1984

[54] PROCESS FOR PRODUCING METHACROLEIN

[75] Inventors: Atsushi Aoshima, Yokohama; Ryoichi Mitsui, Fuji, both of Japan

[73] Assignee: Asahi Kasei Kogyo Kabushiki Kaisha, Osaka, Japan

[21] Appl. No.: 263,667

[22] Filed: May 14, 1981

[30] Foreign Application Priority Data

May 19, 1980 [JP] Japan .................................. 55-66088
May 19, 1980 [JP] Japan .................................. 55-66089

[51] Int. Cl.³ .............................................. C07C 45/32
[52] U.S. Cl. ................................... 568/479; 568/470; 568/471; 568/474; 568/478
[58] Field of Search ............... 568/471, 476, 474, 479, 568/478, 470

[56] References Cited

U.S. PATENT DOCUMENTS

| | | | |
|---|---|---|---|
| 3,660,479 | 5/1972 | Ondrey et al. | 568/479 |
| 3,936,505 | 2/1976 | Oda et al. | 568/479 |
| 4,025,565 | 5/1977 | Oda et al. | 568/479 |
| 4,035,418 | 7/1977 | Okada et al. | 568/479 |
| 4,052,462 | 10/1977 | Sakakibara et al. | 568/479 |
| 4,065,507 | 12/1977 | Hardman et al. | 568/479 |
| 4,258,217 | 3/1981 | Aoshima et al. | 568/474 |
| 4,354,044 | 10/1982 | Aoshima et al. | 568/471 |
| 4,380,664 | 4/1983 | Ishii et al. | 568/471 |

OTHER PUBLICATIONS

Chemical Abstract-abstract of Belgian Pat. No. 623,212, p. 1964, entitled "Aliphatic Compounds".
Hydrocarbon Processing, Nov. 1972, pp. 85-88.

*Primary Examiner*—Werren B. Lone
*Attorney, Agent, or Firm*—Sprung, Horn, Kramer & Woods

[57] ABSTRACT

A process for producing methacrolein by oxidizing isobutylene or tertiary butanol with molecular oxygen, characterized by contacting a gaseous mixture of isobutylene or tertiary butanol, air or oxygen and optionally steam and an inert gas with a catalyst having the general composition:

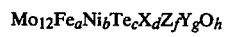

$$Mo_{12}Fe_aNi_bTe_cX_dZ_fY_gO_h$$

wherein a, b, c, d, f and g represent the numbers of atoms of the respective elements per 12 molybdenum atoms; X is Tl, Rb or Cs; Z is In or Ti; Y represents at least one element selected from the group consisting of Cu, Nd, Sm and Pb; a is a value of 0.2-6; b is a value of 0.2-6; a+b is a value of 1-10; c is a value of 0.1-4; d is a value of 0.1-3; f is a value of 0.1-3; g is a value of 0-5; and h is the number of oxygen atoms for satisfying the valencies of the existing elements. The use of this catalyst enables the selectivity for methacrolein to be improved to 90 or more and the yield based on the starting material to be increased to 89-91%. In addition, the high activity of said catalyst and high selectivity are stably maintained for a long period of time.

5 Claims, No Drawings

PROCESS FOR PRODUCING METHACROLEIN

BACKGROUND OF THE INVENTION

1. Field of the Invention

This invention relates to process for producing methacrolein in a high yield by oxidizing isobutylene or tertiary butanol with molecular oxygen with a specific catalyst.

2. Description of the Prior Art

Hitherto, many catalysts have been proposed for the gas phase catalytic oxidation of isobutylene or tertiary butanol. From the industrial point of view, however, there are yet many points to be improved.

For example, in the production of methacrolein, the yield of the product, methacrolein, based on the starting material (isobutylene or tertiary butanol) is still so low that the selectivity based on isobutylene is at most about 82-86% even with a catalyst which has hitherto been called an excellent catalyst. Therefore, a catalyst system capable of giving a much higher selectivity is desired. Some of the catalysts containing molybdenum as a main component and additionally containing tellurium exhibit a considerably high yield in the early stage of the reaction. However, their activities drop markedly owing to structural change and scattering of tellurium, and there has been found substantially no catalyst enabling methacrolein to be obtained in a high yield for a long period of time.

When it is intended to use the resulting methacrolein as a starting material for producing an unsaturated ester directly from an unsaturated aldehyde, it is desired that the amount of by-products such as methacrylic acid and acetic acid is as small as possible. Thus, the use as an industrial catalyst involves a number of problems. The present inventors have conducted earnest and detailed studies with the aim of solving the above-mentioned problems. As a result, this invention has been accomplished.

SUMMARY OF THE INVENTION

According to this invention, there is provided a process for producing methacrolein by oxidizing isobutylene or tertiary butanol with molecular oxygen, characterized by using a catalyst having the general composition:

$$Mo_{12}Fe_aNi_bTe_cX_dZ_fY_gO_h$$

wherein a, b, c, d, f and g represent the numbers of atoms of the respective elements per 12 molybdenum atoms; X is Tl, Rb or Cs; Z is In or Ti; Y represents at least one element selected from the group consisting of Cu, Nd, Sm and Pb; a is a value of 0.2-6; b is a value of 0.2-6; a+b is a value of 1-10; c is a value of 0.1-4; d is a value of 0.1-3; f is a value of 0.1-3; g is a value of 0-5; and h is the number of oxygen atoms for satisfying the valencies of the existing elements.

DETAILED DESCRIPTION OF THE INVENTION

The characteristic feature of this invention consists in that, by the use of said catalyst, the selectivity for methacrolein is as high as 90% or more and methacrolein is obtained from isobutylene or tertiary butanol with a high selectivity. Accordingly, the amounts of methacrylic acid, acetic acid, acetone, carbon monoxide and carbon dioxide, which are by-products, are small. Further, said catalyst exhibits only a very small drop in activity and has an ability to maintain a high activity and a high selectivity for a long period of time.

In the catalyst of this invention, molybdenum is an essential component. A system having the catalyst composition from which molybdenum has been excluded has so low an activity that no improvement in yield of methacrolein is expected.

Tellurium is used as a promotor. Tellurium as a promoter has hitherto been used for improving the catalyst activity and selectivity. However, catalysts containing tellurium have hitherto been regarded as impractical because their activity decreases rapidly, even though they are excellent in initial activity and selectivity.

In this invention, for the purpose of preventing the decrease in catalytic activity which is one of the faluts of catalysts in which tellurium is used as a promotor and imparting a high acitivity, indium or titanium is contained together with iron and nickel in the catalyst system of this invention.

The decrease in catalytic activity is fatal to an industrial catalyst, but can be prevented by using appropriate quantities of indium or titanium and iron and nickel. The above-mentioned effects of indium or titanium and iron and nickel are lost when any one of them is omitted. Moreover, when the contents of iron and nickel are such that the total amount of iron and nickel are larger than the amount of molybdenum, the function of the molybdenum as main catalyst is affected, and this is not desirable.

The addition of indium or titanium brings about not only the above-mentioned effects, but also the effect that the amount of water-soluble acids (acetic acid and methacrylic acid) formed as by-products is particularly made small. Accordingly, the amount of waste water to be treated becomes small, and equippment for treating waste water can be made small, though there has hitherto been required an operation for removing the water-soluble acids and the like from the reaction product gas by means of a quenching tower or the like. Furthermore, when said catalyst is used in the process for producing methacrolein which is a starting material for preparing an unsaturated ester, for example, methyl methacrylate, directly from methacrolein, the amount of methacrylic acid formed as by-product is very small, and therefore, the yield of methacrolein becomes high and the cost for treating the methacrylic acid becomes very low.

As a carrier for the catalyst of this invention, known carriers such as silica, silicon carbide, alumina and the like may be used, among which silica sol and silica gel are particularly excellent. The catalyst of this invention can be prepared, for example, in the following manner: Water-soluble compounds of iron, nickel and the X component, a compound of indium or titanium and a water-soluble Y component compound are added to an aqueous solution of ammonium molybdate, and an oxide or an acid of tellurium is added to the resulting mixture. Furthermore, silica sol is added thereto as a carrier. The mixture is evaporated to dryness on a water bath, preliminarily calcined in the presence of air or oxygen and subsequently subjected to main calcination. Usually, the preliminary calcination is carried out at a temperature of 100°-500° C., preferably 200°-400° C. The main calcination is usually carried out at a temperature of 400°-1,000° C., preferably 500°-700° C., more preferably 500°-650° C.

As the starting materials of the respective elements used in the preparation of the catalyst of this invention, there may be used not only oxides but also any substances so far as they constitute the catalyst of this invention upon being calcined. Examples of said substances include ammonium salts, inorganic acid salts such as nitrate, carbonate and the like and organic acid salts such as acetate and the like, of the above-mentioned elements. The catalyst may be used either in the form of powder, or in a granular form, or as tablet.

As the reactor, either fixed bed or fluidized bed may be used. The reaction of this invention is carried out at a temperature ranging from 200° C. to 550° C., preferably from 250° C. to 450° C. at a pressure of 0.5-10 atmospheres, preferably a pressure ranging from atmospheric pressure to 2 atmospheres.

The contact time between said catalyst and the starting gaseous mixture comprising isobutylene or tertiary butanol, air (or oxygen), steam and an inert gas is 0.1 to 15 seconds, preferably 0.2 to 10 seconds, in the case of atmospheric pressure. The flow rate of the starting gas fed to the catalyst is generally a space velocity of 100 to 5,000 $hr^{-1}$, preferably 200 to 2,000 $hr^{-1}$.

The gaseous mixture comprises 0.5 to 4 moles, preferably 1.4 to 2.5 moles, of oxygen per mole of isobutylene or tertiary butanol. Though steam is not essential, it is advantageous in the aspect of yield to add steam in an amount of 1 to 30 moles, preferably 2 to 15 moles, per mole of isobutylene or tertiary butanol. Moreover, the addition of an inert gas, such as $N_2$, He, Ar, $CO_2$ or the like, may be varied depending upon the variation of the composition of other components.

By using the catalyst of this invention described above in detail, the selectivity for methacrolein reaches even 90-94%. A catalyst capable of giving such a high selectivity and maintaining its activity stably for a long period of time is very epoch-making.

DESCRIPTION OF PREFERRED EMBODIMENTS

This invention is further explained in more detail below referring to Examples, which are merely by way of illustration and not be way of limitation.

3.55 g of indium nitrate and 4.55 g of telluric acid. The resulting solution was mixed with Solution A, to which 52.43 g of silica sol (Snowtex N 30) was added.

Then, this mixture was evaporated to dryness on a water bath, after which the residue was preliminarily calcined in the presence of air at 250° C. for 2 hours, and the calcined product was pulverized to 10-28 meshes and then calcined in the presence of air at 650° C. for 4 hours. The catalyst thus obtained had the following composition:

$Mo_{12}Pb_2Fe_1Ni_1Tl_{0.3}In_1Te_2O_h$.

EXAMPLE 2

A Pyrex reaction tube having an inner diameter of 5 mm was packed with 5 g of the catalyst prepared in Example 1, and reaction was carried out at a reaction temperature of 360° C.–440° C. The starting gas had a molar ratio of isobutylene/$O_2$/$H_2O$/He=3/6/20/71. The contact time was 2.5 seconds. The analysis was carried out with Shimazu 6APrTF Gas Chromatograph, using the Chromosorb 101 column. The results are shown in Table 1.

EXAMPLE 3

Using a catalyst having the composition $Mo_{12}Cu_1Tl_{0.3}Ni_1Fe_1In_{0.3}Te_2O_h$ prepared under the same preparative conditions as in Example 1, reaction was carried out under the same reaction conditions as in Example 2. The results are shown in Table 1.

Comparative Example 1

Using a catalyst having the composition $Mo_{12}Cu_1Tl_{0.3}Fe_1Ni_1Te_2O_h$ prepared under the same preparative conditions as in Example 1, reaction was carried out under the same reaction conditions as in Example 3. The results are shown in Table 1.

EXAMPLE 4

Using a catalyst having the composition $Mo_{12}Cu_1Tl_{0.3}Ni_1Fe_1In_1Te_2O_h$ prepared under the same preparative conditions as in Example 1, reaction was carried out under the same reaction conditions as in Example 2. The results are shown in Table 1.

TABLE 1

| No. | Composition of catalyst | Temperature (°C.) | Conversion of isobutylene (%) | Selectivity for methacrolein (%) | Selectivity for acetic acid plus MAA (%) |
| --- | --- | --- | --- | --- | --- |
| Example 2 | $Mo_{12}Pb_2Fe_1Ni_1Tl_{0.3}In_1Te_2O_h$ | 400 | 93.2 | 93.0 | 0.6 |
| Example 3 | $Mo_{12}Cu_1Tl_{0.3}Fe_1Ni_1In_{0.3}Te_2O_h$ | 380 | 94.3 | 91.5 | 0.8 |
| Example 4 | $Mo_{12}Cu_1Tl_{0.3}Fe_1Ni_1In_1Te_2O_h$ | 380 | 96.4 | 91.0 | 0.7 |
| Comparative Example 1 | $Mo_{12}Cu_1Tl_{0.3}Fe_1Ni_1Te_2O_h$ | 420 | 65.8 | 88.0 | 2.3 |

EXAMPLE 1

In 200 ml of distilled water was dissolved 21.2 g of ammonium paramolybdate, and 0.80 g of thallium nitrate was further dissolved therein. The resulting solution is hereinafter referred to as "Solution A". On the other hand, 2.9 g of nickel nitrate was dissolved in 200 ml of distilled water, and in the resulting solution were discolved 4.04 g of ferric nitrate, 6.6 g of lead nitrate,

EXAMPLES 5–23

Using catalysts having the compositions shown in Table 2 which had been prepared under the same preparative conditions as in Example 1, reactions were carried out under the same reaction conditions as in Example 2. The results are shown in Table 2.

TABLE 2

| Example No. | Composition of catalyst | Temperature (°C.) | Conversion of isobutylene (%) | Selectivity for methacrolein (%) |
|---|---|---|---|---|
| 5 | $Mo_{12}Fe_1Ni_1Tl_{0.3}In_{0.5}Te_2O_h$ | 380 | 95.2 | 91.4 |
| 6 | $Mo_{12}Fe_4Ni_1Tl_{0.3}Pb_2In_{0.5}Te_2O_h$ | 420 | 92.2 | 92.7 |
| 7 | $Mo_{12}Fe_4Ni_1Tl_{0.3}Cu_1In_{0.5}Te_2O_h$ | 410 | 94.3 | 91.0 |
| 8 | $Mo_{12}Fe_2Ni_2Tl_{0.3}Cu_1In_{0.5}Te_2O_h$ | 400 | 95.0 | 91.2 |
| 9 | $Mo_{12}Fe_1Ni_1Rb_{0.3}Cu_1In_{0.5}Te_2O_h$ | 380 | 95.8 | 91.5 |
| 10 | $Mo_{12}Fe_1Ni_1Cs_{0.3}Pb_2In_{0.5}Te_2O_h$ | 400 | 96.2 | 91.0 |
| 11 | $Mo_{12}Fe_1Ni_1Rb_{0.3}Pb_2In_{0.5}Te_2O_h$ | 400 | 97.2 | 90.9 |
| 12 | $Mo_{12}Fe_1Ni_1Tl_1Pb_2In_{0.5}Te_2O_h$ | 400 | 97.4 | 90.7 |
| 13 | $Mo_{12}Fe_1Ni_1Tl_{0.3}Sm_1In_{0.5}Te_2O_h$ | 400 | 91.0 | 91.3 |
| 14 | $Mo_{12}Fe_1Ni_1Tl_{0.3}Cu_1Pb_2In_{0.5}Te_2O_h$ | 380 | 96.5 | 91.5 |
| 15 | $Mo_{12}Fe_1Ni_1Tl_{0.3}Nd_1In_{0.5}Te_2O_h$ | 400 | 92.8 | 92.3 |
| 16 | $Mo_{12}Fe_1Ni_1Tl_{0.3}Nd_1Pb_2In_{0.5}Te_2O_h$ | 400 | 90.9 | 92.0 |
| 17 | $Mo_{12}Fe_1Ni_1Tl_{0.3}Sm_1Pb_2In_{0.5}Te_2O_h$ | 400 | 90.4 | 92.5 |
| 18 | $Mo_{12}Fe_4Ni_4Tl_{0.3}Cu_1In_{0.5}Te_2O_h$ | 420 | 91.4 | 92.0 |
| 19 | $Mo_{12}Fe_1Ni_1Tl_{0.3}Cu_1In_{0.5}Te_4O_h$ | 380 | 96.2 | 92.3 |
| 20 | $Mo_{12}Fe_1Ni_1Tl_{0.3}Cu_1In_{0.5}Te_1O_h$ | 410 | 94.4 | 90.8 |
| 21 | $Mo_{12}Fe_1Ni_1Tl_{0.3}In_3Te_2O_h$ | 420 | 96.1 | 90.9 |
| 22 | $Mo_{12}Fe_1Ni_4Tl_{0.3}Cu_1In_1Te_2O_h$ | 370 | 97.1 | 90.3 |
| 23 | $Mo_{12}Fe_1Ni_1Tl_{0.3}Pb_2Cu_1In_{0.2}Te_2O_h$ | 380 | 96.4 | 92.0 |

Comparative Examples 2-9

Using catalysts having the compositions shown in Table 3 which had been prepared under the same preparative conditions as in Example 1, reactions were carried out under the same reaction conditions as in Example 2. The results are shown in Table 3.

TABLE 3

| Comparative Example No. | Composition of catalyst | Temperature (°C.) | Conversion of isobutylene (%) | Selectivity for methacrolein (%) |
|---|---|---|---|---|
| 2 | $Mo_{12}Fe_1Ni_1Te_2Cu_1In_{0.3}O_h$ | 400 | 97.2 | 81.2 |
| 3 | $Mo_{12}Fe_1Ni_1Te_2Cu_1In_{0.3}Na_{0.3}O_h$ | 400 | 95.1 | 82.3 |
| 4 | $Mo_{12}Fe_{0.2}Ni_{0.2}Te_2Cu_1In_{0.3}Tl_{0.3}O_h$ | 420 | 67.3 | 86.7 |
| 5 | $Mo_{12}Fe_1Te_2Cu_1In_{0.3}Tl_{0.3}O_h$ | 400 | 53.0 | 85.0 |
| 6 | $Mo_{12}Fe_9Ni_4Te_2Cu_1In_{0.3}Tl_{0.3}O_h$ | 400 | 61.4 | 80.4 |
| 7 | $Mo_{12}Fe_1Ni_1Te_6Cu_1In_{0.3}Tl_{0.3}O_h$ | 400 | 91.0 | 86.5 |
| 8 | $Mo_{12}Fe_1Ni_1Te_2Cu_1In_6Tl_{0.3}O_h$ | 420 | 62.3 | 81.7 |
| 9 | $Fe_1Ni_1Te_4Cu_1In_{0.3}Tl_{0.3}O_h$ | 420 | 12.1 | 47.2 |

EXAMPLES 24-26

Using the same catalysts as used in Examples 2-4, reactions were carried out continuously for 100 hours under the same conditions as in the respective Examples. The results are shown in Table 4.

Comparative Example 10

Using a catalyst having the composition shown in Table 5 which had been prepared under the same preparative conditions as in Example 1, reaction was carried out under the same reaction conditions as in Exam-

TABLE 4

| | | | At the start of measurement | | After 100 hours | |
|---|---|---|---|---|---|---|
| Example No. | Composition of catalyst | Temperature (°C.) | Conversion of isobutylene (%) | Selectivity for methacrolein (%) | Conversion of isobutylene (%) | Selectivity for methacrolein (%) |
| 24 | $Mo_{12}Pb_2Tl_{0.3}Fe_1Ni_1In_1Te_2O_h$ | 400 | 93.2 | 93.0 | 93.2 | 93.0 |
| 25 | $Mo_{12}Cu_1Tl_{0.3}Fe_1Ni_1In_{0.3}Te_2O_h$ | 380 | 94.3 | 91.5 | 94.4 | 91.3 |
| 26 | $Mo_{12}Cu_1Tl_{0.3}Fe_1Ni_1In_1Te_2O_h$ | 380 | 96.4 | 91.0 | 96.4 | 91.1 |

EXAMPLES 27-29

A Pyrex reaction tube having an inner diameter of 5 mm was packed with 5 g of each of the catalysts having the compositions shown in Table 5 which had been prepared under the same preparative conditions as in Example 1, and reactions were carried out at a reaction temperature of 380°-440° C.

The starting gas had a molar ratio of tertiary butanol/$O_2$/$H_2O$/He=3/6/20/71. The contact time was 2.5 seconds. The results are shown in Table 5.

ples 27-29. The results are shown in Table 5.

TABLE 5

| No. | Composition of catalyst | Temperature (°C.) | Conversion of isobutylene (%) | Selectivity for methacrolein (%) | Selectivity for acetic acid plus methacrylic acid (%) |
| --- | --- | --- | --- | --- | --- |
| Example 27 | $Mo_{12}Fe_1Ni_1Pb_2Tl_{0.3}In_1Te_2O_h$ | 400 | 93.0 | 93.0 | 0.7 |
| Example 28 | $Mo_{12}Fe_1Ni_1Cu_1Tl_{0.3}In_{0.3}Te_2O_h$ | 380 | 94.3 | 91.6 | 0.8 |
| Example 29 | $Mo_{12}Fe_1Ni_1Cu_1Tl_{0.3}In_1Te_2O_h$ | 380 | 96.3 | 91.0 | 0.7 |
| Comparative Example 10 | $Mo_{12}Fe_1Ni_1Cu_1Tl_{0.3}Te_2O_h$ | 380 | 65.8 | 87.8 | 2.6 |

EXAMPLES 30–48

Using catalysts having the compositions shown in Table 6 which had been prepared under the same preparative conditions as in Example 1, reactions were carried out under the same reaction conditions as in Examples 27–29. The results are shown in Table 6.

TABLE 6

| Example No. | Composition of catalyst | Temperature (°C.) | Conversion of isobutylene (%) | Selectivity for methacrolein (%) |
| --- | --- | --- | --- | --- |
| 30 | $Mo_{12}Fe_1Ni_1Tl_{0.3}In_{0.5}Te_2O_h$ | 380 | 95.0 | 91.5 |
| 31 | $Mo_{12}Fe_4Ni_1Tl_{0.3}Pb_2In_{0.5}Te_2O_h$ | 420 | 92.2 | 92.5 |
| 32 | $Mo_{12}Fe_4Ni_1Tl_{0.3}Cu_1In_{0.5}Te_2O_h$ | 410 | 94.4 | 90.8 |
| 33 | $Mo_{12}Fe_2Ni_2Tl_{0.3}Cu_1In_{0.5}Te_2O_h$ | 400 | 94.8 | 91.3 |
| 34 | $Mo_{12}Fe_1Ni_1Rb_{0.3}Cu_1In_{0.5}Te_2O_h$ | 380 | 95.7 | 91.5 |
| 35 | $Mo_{12}Fe_1Ni_1Cs_{0.3}Pb_2In_{0.5}Te_2O_h$ | 400 | 96.1 | 91.0 |
| 36 | $Mo_{12}Fe_1Ni_1Rb_{0.3}Pb_2In_{0.5}Te_2O_h$ | 400 | 97.0 | 90.6 |
| 37 | $Mo_{12}Fe_1Ni_1Tl_1Pb_2In_{0.5}Te_2O_h$ | 400 | 97.3 | 90.8 |
| 38 | $Mo_{12}Fe_1Ni_1Tl_{0.3}Sm_1In_{0.5}Te_2O_h$ | 400 | 91.0 | 91.4 |
| 39 | $Mo_{12}Fe_1Ni_1Tl_{0.3}Cu_1Pb_2In_{0.5}Te_2O_h$ | 380 | 96.3 | 91.0 |
| 40 | $Mo_{12}Fe_1Ni_1Tl_{0.3}Nd_1In_{0.5}Te_2O_h$ | 400 | 92.7 | 92.3 |
| 41 | $Mo_{12}Fe_1Ni_1Tl_{0.3}Nd_1Pb_2In_{0.5}Te_2O_h$ | 400 | 90.7 | 92.1 |
| 42 | $Mo_{12}Fe_1Ni_1Tl_{0.3}Sm_1Pb_2In_{0.5}Te_2O_h$ | 400 | 90.5 | 92.4 |
| 43 | $Mo_{12}Fe_4Ni_4Tl_{0.3}Cu_1In_{0.5}Te_2O_h$ | 420 | 91.0 | 92.1 |
| 44 | $Mo_{12}Fe_1Ni_1Tl_{0.3}Cu_1In_{0.5}Te_4O_h$ | 380 | 96.1 | 92.5 |
| 45 | $Mo_{12}Fe_1Ni_1Tl_{0.3}Cu_1In_{0.5}Te_1O_h$ | 410 | 94.1 | 90.0 |
| 46 | $Mo_{12}Fe_1Ni_1Tl_{0.3}Cu_1In_3Te_2O_h$ | 420 | 95.7 | 90.9 |
| 47 | $Mo_{12}Fe_1Ni_4Tl_{0.3}Cu_1In_1Te_2O_h$ | 370 | 97.0 | 90.1 |
| 48 | $Mo_{12}Fe_1Ni_1Tl_{0.3}Pb_2Cu_1In_{0.2}Te_2O_h$ | 380 | 96.4 | 91.8 |

Comparative Examples 11–17

Using catalysts having the compositions shown in Table 7 which had been prepared under the same preparative conditions as in Example 1, reactions were carried out under the same reaction conditions as in Examples 27–29. The results are shown in Table 7.

TABLE 7

| Comparative Example No. | Composition of catalyst | Temperature (°C.) | Conversion of t-BuOH (%) | Selectivity for methacrolein (%) |
| --- | --- | --- | --- | --- |
| 11 | $Mo_{12}Fe_1Ni_1Cu_1In_{0.3}Te_2O_h$ | 400 | 97.0 | 81.3 |
| 12 | $Mo_{12}Fe_1Ni_1Cu_1In_{0.3}Na_{0.3}Te_2O_h$ | 400 | 95.1 | 82.0 |
| 13 | $Mo_{12}Fe_{0.2}Ni_{0.2}Tl_{0.5}Cu_1In_{0.3}Te_2O_h$ | 420 | 67.2 | 87.6 |
| 14 | $Mo_{12}Fe_1Tl_{0.3}Cu_1In_{0.3}Te_2O_h$ | 400 | 53.0 | 85.1 |
| 15 | $Mo_{12}Fe_9Ni_4Tl_{0.3}Cu_1In_{0.3}Te_2O_h$ | 400 | 61.0 | 80.3 |
| 16 | $Mo_{12}Fe_1Ni_1Tl_{0.3}Cu_1In_{0.3}Te_2O_h$ | 400 | 90.6 | 86.6 |
| 17 | $Mo_{12}Fe_1Ni_1Tl_{0.3}Cu_1In_6Te_2O_h$ | 420 | 62.3 | 82.0 |

EXAMPLES 49–51

Using the same catalysts as in Examples 2–4, reactions were carried out continuously for 100 hours under the same conditions as in the respective Examples. The results are shown in Table 8.

TABLE 8

| | | | At the start of measurement | | After 100 hours | |
| --- | --- | --- | --- | --- | --- | --- |
| Example No. | Composition of catalyst | Temperature (°C.) | Conversion of isobutylene (%) | Selectivity for methacrolein (%) | Conversion of isobutylene (%) | Selectivity for methacrolein (%) |
| 49 | $Mo_{12}Pb_2Tl_{0.3}Fe_1Ni_1In_1Te_2O_h$ | 400 | 93.0 | 93.0 | 93.1 | 93.0 |

TABLE 8-continued

| | | | At the start of measurement | | After 100 hours | |
|---|---|---|---|---|---|---|
| Example No. | Composition of catalyst | Temperature (°C.) | Conversion of isobutylene (%) | Selectivity for methacrolein (%) | Conversion of isobutylene (%) | Selectivity for methacrolein (%) |
| 50 | $Mo_{12}Cu_1Tl_{0.3}Fe_1Ni_1In_{0.3}Te_2O_h$ | 380 | 94.3 | 91.6 | 94.3 | 91.4 |
| 51 | $Mo_{12}Cu_1Tl_{0.3}Fe_1Ni_1In_1Te_2O_h$ | 380 | 96.3 | 91.0 | 96.3 | 91.0 |

EXAMPLE 52

In 200 ml of distilled water was dissolved 21.2 g of ammonium paramolybdate, and 0.80 g of thallium nitrate was then dissolved in the resulting solution. The resulting solution is hereinafter referred to as "Solution A". On the other hand, 2.9 g of nickel nitrate was dissolved in 200 ml of distilled water, and in the resulting solution were dissolved 4.04 g of ferric nitrate, 6.6 g of lead nitrate, 1.54 g of titanium trichloride and 4.55 g of telluric acid. The resulting solution was mixed with Solution A, to which 52.43 g of silica sol (Snowtex) was added thereto.

Then, this mixture was evaporated to dryness on a water bath, and the residue was preliminarily calcined in the presence of air at 250° C. for 2 hours. The calcined product was pulverized to 10–28 meshes and then calcined in the presence of air at 650° C. for 4 hours. The catalyst thus obtained had the following composition:

$Mo_{12}Pb_2Fe_1Ni_1Tl_{0.3}Ti_1Te_2O_h$.

EXAMPLE 53

A Pyrex reaction tube having an inner diameter of 5 mm was packed with 5 g of the catalyst prepared in Example 52, and reaction was carried out therein at a reaction temperature of 400° C. The starting gas had a molar ratio of isobutylene/$O_2$/$H_2O$/He = 3/6/20/71. The contact time was 2.5 seconds. The analysis was carried out with Shimazu 6APrTF Gas Chromatograph, using a Chromosorb 101 column. The results are shown in Table 9.

EXAMPLES 54–55

Using catalysts having the compositions shown in Table 9 which had been prepared under the same preparative conditions as in Example 52, reactions were carried out under the same reaction conditions as in Example 53. The results are shown in Table 9.

TABLE 9

| Example No. | Composition of catalyst | Temperature (°C.) | Conversion of isobutylene (%) | Selectivity for methacrolein (%) | Selectivity for acetic acid plus methacrylic acid (%) |
|---|---|---|---|---|---|
| 53 | $Mo_{12}Pb_2Fe_1Ni_1Tl_{0.3}Ti_1Te_2O_h$ | 400 | 93.5 | 92.8 | 0.7 |
| 54 | $Mo_{12}Cu_1Tl_{0.3}Fe_1Ni_1Tl_{0.3}Te_2O_h$ | 380 | 94.8 | 91.4 | 0.7 |
| 55 | $Mo_{12}Cu_1Fe_1Ni_1Ti_1Tl_{0.3}Te_2O_h$ | 380 | 96.7 | 90.9 | 0.8 |

EXAMPLES 56–74

Using catalysts having the compositions shown in Table 10 which had been prepared under the same preparative conditions as in Example 52, reactions were carried out under the same reaction conditions as in Example 53. The results are shown in Table 10.

TABLE 10

| Example No. | Composition of catalyst | Temperature (°C.) | Conversion of isobutylene (%) | Selectivity for methacrolein (%) |
|---|---|---|---|---|
| 56 | $Mo_{12}Fe_1Ni_1Tl_{0.3}Ti_{0.5}Te_2O_h$ | 380 | 96.0 | 90.9 |
| 57 | $Mo_{12}Fe_4Ni_1Tl_{0.3}Pb_2Ti_{0.5}Te_2O_h$ | 420 | 93.1 | 92.0 |
| 58 | $Mo_{12}Fe_4Ni_1Tl_{0.3}Cu_1Ti_{0.5}Te_2O_h$ | 410 | 94.8 | 90.5 |
| 59 | $Mo_{12}Fe_2Ni_2Tl_{0.3}Cu_1Ti_{0.5}Te_2O_h$ | 400 | 95.8 | 91.0 |
| 60 | $Mo_{12}Fe_1Ni_1Rb_{0.3}Cu_1Ti_{0.5}Te_2O_h$ | 380 | 96.2 | 91.1 |
| 61 | $Mo_{12}Fe_1Ni_1Cs_{0.3}Pb_2Ti_{0.5}Te_2O_h$ | 400 | 96.8 | 90.8 |
| 62 | $Mo_{12}Fe_1Ni_1Rb_{0.3}Pb_2Ti_{0.5}Te_2O_h$ | 400 | 98.0 | 90.1 |
| 63 | $Mo_{12}Fe_1Ni_1Tl_1Pb_1Ti_{0.5}Te_2O_h$ | 400 | 97.7 | 90.5 |
| 64 | $Mo_{12}Fe_1Ni_1Tl_{0.3}Sm_1Ti_{0.5}Te_2O_h$ | 400 | 92.2 | 91.0 |
| 65 | $Mo_{12}Fe_1Ni_1Tl_{0.3}Cu_1Pb_2Ti_{0.5}Te_2O_h$ | 380 | 97.0 | 90.9 |
| 66 | $Mo_{12}Fe_1Ni_1Tl_{0.3}Nd_1Te_{0.3}Te_2O_h$ | 400 | 93.3 | 92.0 |
| 67 | $Mo_{12}Fe_1Ni_1Tl_{0.3}Nd_1Pb_2Ti_{0.5}Te_2O_h$ | 400 | 92.0 | 91.1 |
| 68 | $Mo_{12}Fe_1Ni_1Tl_{0.3}Sm_1Pb_2Ti_{0.5}Te_2O_h$ | 400 | 91.6 | 92.0 |
| 69 | $Mo_{12}Fe_4Ni_4Tl_{0.3}Cu_1Ti_{0.5}Te_2O_h$ | 420 | 93.2 | 90.9 |
| 70 | $Mo_{12}Fe_1Ni_1Tl_{0.3}Cu_1Ti_{0.5}Te_4O_h$ | 380 | 96.5 | 91.8 |
| 71 | $Mo_{12}Fe_1Ni_1Tl_{0.3}Cu_1Ti_{0.5}Te_1O_h$ | 410 | 95.3 | 90.5 |
| 72 | $Mo_{12}Fe_1Ni_1Tl_{0.3}Ti_3Te_2O_h$ | 420 | 96.6 | 90.2 |
| 73 | $Mo_{12}Fe_1Ni_4Tl_{0.3}Cu_1Ti_1Te_2O_h$ | 370 | 97.6 | 90.1 |
| 74 | $Mo_{12}Fe_1Ni_1Tl_{0.3}Pb_2Cu_1Ti_{0.2}Te_2O_h$ | 380 | 96.6 | 91.5 |

Comparative Examples 18–25

Using catalysts having the compositions shown in Table 11 which had been prepared under the same preparative conditions as in Example 52, reactions were carried out under the same reaction conditions as in Example 53. The results are shown in Table 11.

prepared under the same preparative conditions as in Example 52, and reactions were carried out at a reaction

TABLE 11

| Comparative Example No. | Composition of catalyst | Temperature (°C.) | Conversion of isobutylene (%) | Selectivity for methacrolein (%) |
|---|---|---|---|---|
| 18 | $Mo_{12}Fe_1Ni_1Te_2Cu_1Tl_{0.3}O_h$ | 400 | 97.4 | 81.0 |
| 19 | $Mo_{12}Fe_1Ni_1Na_{0.3}Te_2Cu_1Tl_{0.3}O_h$ | 400 | 95.3 | 82.2 |
| 20 | $Mo_{12}Fe_{0.2}Ni_{0.2}Tl_{0.3}Te_2Cu_1Ti_{0.3}O_h$ | 420 | 67.3 | 86.7 |
| 21 | $Mo_{12}Fe_1Tl_{0.3}Te_2Cu_1Ti_{0.3}O_h$ | 400 | 53.5 | 85.2 |
| 22 | $Mo_{12}Fe_9Ni_4Tl_{0.3}Te_2Cu_1Ti_{0.3}O_h$ | 400 | 61.4 | 79.9 |
| 23 | $Mo_{12}Fe_1Ni_1Tl_{0.3}Te_6Cu_1Ti_{0.3}O_h$ | 400 | 91.5 | 86.3 |
| 24 | $Mo_{12}Fe_1Ni_1Tl_{0.3}Te_2Cu_1Ti_6O_h$ | 420 | 62.8 | 81.3 |
| 25 | $Fe_1Ni_1Te_4Cu_1Ti_{0.3}Tl_{0.3}O_h$ | 420 | 12.9 | 46.0 |

EXAMPLES 75–77

Using the same catalysts as used in Examples 53–54, reactions were carried out continuously for 100 hours temperature of 380°–440° C.

The starting gas had a molar ratio of tertiary butanol/$O_2$/$H_2O$/He = 3/6/20/71. The contact time was 2.5 seconds. The results are shown in Table 13.

TABLE 13

| Example No. | Composition of catalyst | Temperature (°C.) | Conversion of t-BuOH (%) | Selectivity for methacrolein (%) | Selectivity for acetic acid plus methacrylic acid (%) |
|---|---|---|---|---|---|
| 78 | $Mo_{12}Pb_2Fe_1Ni_1Tl_{0.3}Ti_1Te_2O_h$ | 400 | 93.3 | 92.8 | 0.8 |
| 79 | $Mo_{12}Cu_1Fe_1Ni_1Tl_{0.3}Ti_{0.3}Te_2O_h$ | 380 | 94.5 | 91.6 | 0.8 |
| 80 | $Mo_{12}Cu_1Fe_1Ni_1Tl_{0.3}Ti_1Te_2O_h$ | 380 | 96.7 | 90.9 | 0.9 | under the same reaction conditions as in the respective Examples. The results are shown Table 12.

EXAMPLES 81–99

TABLE 12

| | | | At the start of measurement | | After 100 hours | |
|---|---|---|---|---|---|---|
| Example No. | Composition of catalyst | Temperature (°C.) | Conversion of isobutylene (%) | Selectivity for methacrolein (%) | Conversion of isobutylene (%) | Selectivity for methacrolein (%) |
| 75 | $Mo_{12}Pb_2Tl_{0.3}Fe_1Ni_1Ti_1Te_2O_h$ | 400 | 93.5 | 92.8 | 93.4 | 92.8 |
| 76 | $Mo_{12}Cu_1Tl_{0.3}Fe_1Ni_1Ti_{0.3}Te_2O_h$ | 380 | 94.8 | 91.4 | 94.9 | 91.4 |
| 77 | $Mo_{12}Cu_1Tl_{0.3}Fe_1Ni_1Ti_1Te_2O_h$ | 380 | 96.7 | 90.9 | 96.7 | 90.9 |

EXAMPLES 78–80

A Pyrex reaction tube having an inner diameter of 5 mm was packed with 5 g of each of the catalysts having the compositions shown in Table 13 which had been Using catalysts having the compositions shown in Table 14 which had been prepared under the same preparative conditions as in Example 52, reactions were carried out under the same reaction conditions as in Examples 78–80. The results are shown in Table 14.

TABLE 14

| Example No. | Composition of catalyst | Temperature (°C.) | Conversion of t-BuOH (%) | Selectivity for methacrylic acid (%) |
|---|---|---|---|---|
| 81 | $Mo_{12}Fe_1Ni_1Tl_{0.3}Ti_{0.5}Te_2O_h$ | 380 | 95.8 | 90.9 |
| 82 | $Mo_{12}Fe_4Ni_1Tl_{0.3}Pb_2Ti_{0.5}Te_2O_h$ | 420 | 93.1 | 91.8 |
| 83 | $Mo_{12}Fe_4Ni_1Tl_{0.3}Cu_1Ti_{0.5}Te_2O_h$ | 410 | 94.5 | 90.6 |
| 84 | $Mo_{12}Fe_2Ni_2Tl_{0.3}Cu_1Ti_{0.5}Te_2O_h$ | 400 | 95.5 | 91.1 |
| 85 | $Mo_{12}Fe_1Ni_1Rb_{0.3}Cu_1Ti_{0.5}Te_2O_h$ | 380 | 96.0 | 91.3 |
| 86 | $Mo_{12}Fe_1Ni_1Cs_{0.3}Pb_2Ti_{0.5}Te_2O_h$ | 400 | 96.6 | 90.7 |
| 87 | $Mo_{12}Fe_1Ni_1Rb_{0.3}Pb_2Ti_{0.5}Te_2O_h$ | 400 | 97.8 | 90.3 |
| 88 | $Mo_{12}Fe_1Ni_1Tl_1Pb_1Ti_{0.5}Te_2O_h$ | 400 | 97.6 | 90.5 |
| 89 | $Mo_{12}Fe_1Ni_1Tl_{0.3}Sm_1Ti_{0.5}Te_2O_h$ | 400 | 92.2 | 91.0 |
| 90 | $Mo_{12}Fe_1Ni_1Tl_{0.3}Cu_1Pb_2Ti_{0.5}Te_2O_h$ | 380 | 96.9 | 90.8 |
| 91 | $Mo_{12}Fe_1Ni_1Tl_{0.3}Nd_1Ti_{0.5}Te_2O_h$ | 400 | 93.1 | 92.0 |
| 92 | $Mo_{12}Fe_1Ni_1Tl_{0.3}Nd_1Pb_2Ti_{0.5}Te_2O_h$ | 400 | 92.1 | 91.0 |
| 93 | $Mo_{12}Fe_1Ni_1Tl_{0.3}Sm_1Pb_2Ti_{0.5}Te_2O_h$ | 400 | 91.5 | 92.0 |
| 94 | $Mo_{12}Fe_4Ni_4Tl_{0.3}Cu_1Ti_{0.5}Te_2O_h$ | 420 | 93.1 | 90.9 |
| 95 | $Mo_{12}Fe_1Ni_1Tl_{0.3}Cu_1Ti_{0.5}Te_4O_h$ | 380 | 96.3 | 91.7 |
| 96 | $Mo_{12}Fe_1Ni_1Tl_{0.3}Cu_1Ti_{0.5}Te_1O_h$ | 410 | 95.4 | 90.5 |
| 97 | $Mo_{12}Fe_1Ni_1Tl_{0.3}Cu_1Ti_3Te_2O_h$ | 420 | 96.1 | 90.1 |
| 98 | $Mo_{12}Fe_1Ni_4Tl_{0.3}Cu_1Ti_1Te_2O_h$ | 370 | 97.6 | 90.1 |

TABLE 14-continued

| Example No. | Composition of catalyst | Temperature (°C.) | Conversion of t-BuOH (%) | Selectivity for methacrylic acid (%) |
|---|---|---|---|---|
| 99 | $Mo_{12}Fe_1Ni_1Tl_{0.3}Pb_2Cu_1Ti_{0.2}Te_2O_h$ | 380 | 96.5 | 91.6 |

What we claim:

1. A process for producing methacrolein by oxidizing isobutylene or tertiary butanol with molecular oxygen in the presence of a catalyst, characterized in that the oxidation is conducted at a temperature of 200° to 550° C. at a pressure of 9.5 to 10 atm at a space velocity of 100 to 5,000 $hr^{-1}$ for a contact time of 0.1 to 15 sec and the catalyst has the general composition:

$$Mo_{12}Fe_aNi_bTe_cX_dZ_fY_gO_h$$

wherein a, b, c, d, f and g represent the numbers of atoms of the respective elements per 12 molybdenum atoms; X is Tl, Rb or Cs; Z is In or Ti; Y represents at least one element selected from the group consisting of Cu, Nd, Sm and Pb; a is a value of 0.2-6; b is a value of 0.2-6; a+b is a value of 1-10; c is a value of 0.1-4; d is a value of 0.1-3; f is a value of 0.1-3; g is a value of 0-5; and h is the number of oxygen atoms for satisfying the valencies of the existing elements.

2. A process according to claim 1, wherein said catalyst is supported on a carrier.

3. A process according to claim 2, wherein said carrier is silica, silicon carbide or alumina.

4. A process according to any one of claims 1-3, wherein the reaction is carried out at a temperature of 250°-450° C. at a pressure ranging from normal pressure to 2 atmospheres.

5. A process according to any one of claims 1-3, wherein a gaseous mixture comprising isobutylene or tertiary butanol, air or oxygen, steam and an inert gas is contacted with said catalyst under normal pressure.

* * * * *